United States Patent [19]

Read, Jr. et al.

[11] Patent Number: 5,015,409
[45] Date of Patent: May 14, 1991

[54] VISCOSITY-MODIFIERS FOR AQUEOUS-BASED FUNCTIONAL PRODUCTS CONTAINING MIXED METAL HYDROXIDES

[75] Inventors: Arthur E. Read, Jr.; John L. Burba, III, both of Lake Jackson, Tex.; Peter A. Doty; Clarence R. Crabb, both of Midland, Mich.

[73] Assignee: The Dow Chemical Company, Midland, Mich.

[21] Appl. No.: 166,955

[22] Filed: Mar. 11, 1988

Related U.S. Application Data

[63] Continuation-in-part of Ser. No. 60,133, Jun. 9, 1987, which is a continuation of Ser. No. 752,325, Jul. 5, 1985, abandoned.

[51] Int. Cl.$^5$ ............... C11D 1/12; C09K 3/00; A61K 7/32; A61K 9/00
[52] U.S. Cl. ............... 252/108; 252/89.1; 252/95; 252/96; 252/108; 252/157; 252/186.1; 252/188.1; 252/187.25; 252/188.1; 252/188.21; 252/387; 252/388; 252/389.2; 252/389.23; 252/106; 424/70; 424/73; 424/65; 424/68; 424/401; 424/404

[58] Field of Search ............... 252/101, 89.1, 8.514, 252/315.01, 315.7, 553, 186.1, 188.1, 108

[56] References Cited

FOREIGN PATENT DOCUMENTS 0207811 1/1987 European Pat. Off. .

*Primary Examiner*—Prince E. Willis
*Assistant Examiner*—John F. McNally
*Attorney, Agent, or Firm*—W. J. Lee

[57] ABSTRACT

Aqueous-based functional products or corrosive products such as cleansers, household products, commercial products, and personal care products are thickened or viscosity-modified by the addition of at least a small, but effective, amount of at least one crystalline mixed metal hydroxide conforming substantially to the formula

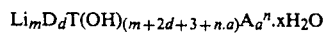

$$Li_m D_d T(OH)_{(m+2d+3+n.a)} A_a^n \cdot xH_2O$$

where m is zero to one, D is a divalent metal, d is from zero to 4, T is a trivalent metal, A represents at least one anion or negative-valence radial of valence n, where n is 1 or more, (m+2d+3+n.a) is equal to or greater than 3, (m+d) is greater than zero, and $xH_2O$ represents excess waters of hydration.

26 Claims, No Drawings

VISCOSITY-MODIFIERS FOR AQUEOUS-BASED FUNCTIONAL PRODUCTS CONTAINING MIXED METAL HYDROXIDES

CROSS-REFERENCE TO RELATED APPLICATION

This is a continuation-in-part of pending application Ser. No. 060,133 filed June 9, 1987 which is, itself, a continuation under 37 CFR 1.60 of Ser. No. 752,325 filed July 5, 1985, now abandoned.

FIELD OF THE INVENTION

Thickeners or viscosity-modifiers for aqueous-based functional products, e.g. cleansers, household products, commercial products, and personal care products are disclosed.

BACKGROUND OF THE INVENTION

Thickeners or other viscosity-modifiers are often used in aqueous-based functional products, e.g. household products, commercial products, cleansers, disinfectants, bleaches, and the like and in personal care products, such as soaps, lotions, face creams, hand creams, toothpaste, and the like. Thickeners that have been used in these applications include such things as natural and synthetic water-sensitive organic polymers, or other water-sensitive organic substances. Also, inorganic substances, such as natural clays, refined clays, synthetic clay-like materials, silicates, and aluminates have been used. As used herein, a "functional" product is one which is applied to, or mixed with, or added to a substance which is desirably and beneficially affected by the thickener, such as cleaning solutions, bleaches, lotions, creams, corrosive fluids, oxidizing agents, reducing agents, alkali solutions, amine solutions, phenolic solutions, and chemical solutions not lower than about pH 4.5 preferably not lower than about pH 5.

Natural clays and refined natural clays may vary from one mining location to another and the performance obtained with one batch may not exactly match the performance of another batch: the color may not match and the effect on viscosity may not match. The natural clays, and even refined natural clays, may contain impurities which can produce non-uniformity among batches and may create side-reactions with other ingredients in a formulation to which the clay is added. Clays are normally anionic and can react with ingredients which are cationic, such as cationic surfactants used in hair conditioners or in cleansers and the like.

Polymers or other organic thickeners are often subject to microbial attack and may lose their effectiveness if not protected with a preservative. Polymerics often have a gooey, tacky, and/or slippery feel on the skin which is unpleasant. Some polymers do not typically have a true yield point which is required to indefinitely suspend solids. Many of the polymeric thickeners also contain functional groups which are adversely attacked by the chemicals in bleaches or other formulations, and this can cause a loss or diminishment of either the desired viscosity control or the effectiveness of the chemical.

SUMMARY OF THE INVENTION

We have now found that certain mixed metal hydroxides, which are of layered crystalline structures exhibiting cationic surface charges, are beneficially employed as thickeners or viscosity-modifiers in various aqueous-based functional products such as various formulations used in cleansers, household products, commercial products, and personal care products. For purposes of conciseness, the expression "MMOH" will be used in this disclosure to refer to the mixed metal hydroxides which are described in detail below. The inorganic MMOH compounds are resistant to microbial attack, are cationic (which prevents interaction with cationic ingredients used in many of the formulations), and, since they are synthetic, can be made substantially of consistent quality and purity.

The crystalline mixed metal hydroxides (MMOH) used in the present invention conform substantially to the empirical formula

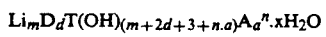

$$Li_m D_d T(OH)_{(m+2d+3+n.a)} A_a^n \cdot xH_2O$$

where m is an amount of Li of from zero to one,
where D represents at least one divalent metal cation and d is an amount of from about zero to about 4,
where T represents at least one trivalent metal cation,
where A represents at least one monovalent or polyvalent anion or negative-valence radical,
a is an amount of A ions of valence n, with n.a being an amount of from about zero to about $-3$,
where (m+2d+3+n.a) is equal to or greater than 3,
where m+d is greater than zero, and
where $xH_2O$ represents excess waters of hydration, with x being zero or more. (By "excess waters of hydration" it is meant that there is more water associated with the compound than is needed to supply the amount of hydroxyl ions required in the crystal formula.)

In the above formula, it should be noted that n, being the valence of the anion, is a negative number: thus n.a is a negative number.

These crystalline mixed metal hydroxides are found to be beneficial as thickeners or viscosity-modifiers for aqueous-based functional products, such as cleansers, commercial products, household products, and personal care products when incorporated therein.

In one aspect, the present invention is perceived as being a formulation of the type described having incorporated therein the MMOH compounds.

In another aspect, the present invention is perceived as a means, method, or process for providing viscosity-modifiers or thickeners to the described formulations by incorporating therein the MMOH compounds.

A further aspect is that MMOH compounds provide a thickened product which thins readily under even very slight shear, but which rethickens rapidly when the shear is stopped. The gelation rate is perceived as being immediate.

In yet another aspect, the present invention is perceived as a beneficial use of the MMOH compounds.

DETAILED DESCRIPTIONS INCLUDING BEST MODE

The MMOH compounds useful in the present invention are preferably those of the monodispersed, monolayer variety such as described in copending Ser. No. 060,133 filed June 9, 1987 and in U.S. Pat. No. 4,664,843, but can also be of the varieties disclosed in U.S. Pat. Nos. 4,477,367; 4,446,201; 4,392,979;and 4,461,714 and the like. For the most part the MMOH compounds are prepared by the general process of forming a solution of compounds of the subject metals under certain conditions whereby a soluble alkaline material, e.g. ammonia or caustic, reacts with the soluble metal compounds to produce the layered crystals of mixed metal hydroxides. However in the present invention, it is often best to avoid having ammonia in the product, in which case another alkaline material, especially NaOH or KOH is used. The MMOH may be used as a slurry of varied solids content, or dry.

The process of using MMOH compounds to thicken aqueous-based functional products can be achieved in at least two general ways. One method, in general, involves the activation of the MMOH particles by an electrolyte. In this process, the MMOH is first dispersed by using high shear, sonic waves or other methods known in the art to produce a high degree of dispersion of agglomerated particles. Once the material is dispersed in aqueous or partially aqueous media, a salt (electrolyte) is added either predissolved or dry and mixing/or shearing is continued until a smooth, thickened system is obtained. Other ingredients may be blended into the prethickened material. Often, one or more of the ingredients is a salt and a separate activator is not needed. The salt used for activation can be almost any ionic substance but components containing organic anions or multivalent anions such as $CO_3^{-2}$, $PO_4^{-3}$, $P_3O_{10}^{-5}$ and the like are usually more effective.

The other general method involves interaction with other colloidal particles in such a manner that they are linked together through bridges or bonds formed by the MMOH. In these cases, it can be interpreted as forming an adduct with the other particles. This can produce an "extension" effect. This can happen, for instance, when fumed silica or a clay is also an ingredient and less material is needed for thickening. This can also occur when a normally soluble material is included in the formulation beyond the point of saturation such that very small or colloidal particles are present as crystals or agglomerates. In this case, the thickening occurs when the MMOH and other particles are sheared together and agglomerates are broken, exposing fresh faces which react.

As used in this disclosure, the expression "thickener" when used in reference to the effect of the MMOH additives, means that the apparent viscosity at ambient conditions and at little or no applied shear has been increased by the addition of the MMOH. The expression "viscosity-modifier" is used herein to refer to the effect obtained by the addition of the MMOH whether or not the effect on viscosity is evident at ambient conditions or at non-ambient conditions and whether or not the effect is a thickening effect apparent under no-stress conditions or under shear. For example, changing of a Newtonian liquid to a non-Newtonian liquid, or vice-versa, is one form of a viscosity modification. Changing the degree or extent of thixotropicity or dilatancy of a liquid is a form of viscosity modification.

The expression "mixed metal hydroxide" implies that there are at least two different metals in the hydrous oxide crystals. In the present invention, it is preferred that at least one of the metals is a trivalent metal, along with at least one other metal which can be either, or both, of the divalent or monovalent (Li) varieties. The amount of the A anion (or negative-valence radical) is that which substantially satisfies the valence requirements of the cations in the crystalline material.

In the above described formula, the trivalent metal cation is preferably Al, Fe, or Ga, and can be mixtures of any of these: Al is most preferred as the trivalent metal.

The divalent metal cation is preferably Mg, Ca, Mn, Fe, Co, Ni, Cu, or Zn and can be mixtures of any of these; Ca or Mg, especially Mg, is most preferred as the divalent metal.

The anion, A, can be monovalent, divalent, trivalent, or polyvalent, and is preferably at least one selected from the group consisting of hydroxyl, halide, sulfate, nitrate, phosphate, carbonate, glycolate, lignosulfate, and polycarboxylic or negative-valence radicals. Thus, the A anion can be inorganic or a hydrophilic organic group. Preferably the A anion is inorganic.

The contents of the numerous formulations that can be thickened or modified by the addition of MMOH compounds can be varied widely. Generally, the ingredients and levels of the ingredients which are in a given formulation have more to do with a desired effect other than that of thickening or viscosity-modification. The versatility of the MMOH compounds is beneficial in that it can be added to so many formulations for viscosity purposes without interfering with the other ingredients in their intended purpose. Substitutions, replacements, and/or eliminations of one or more of the components (other than the MMOH compound) usually has little effect on thickening or viscosity-modification.

The amount of the MMOH added to the aqueous-based functional product formulation, cleanser, household product, commercial product, or personal care product and the like will usually be an amount in the range of about 0.03% to 10% or more depending somewhat on the temperature, on the product into which it is added, on which of the MMOH varieties is being used, and on the extent of thickening or viscosity-modification desired. Speaking in a general sense, one would probably use about 0.5% to about 5%, and may find the range of about 1% to about 2% to most preferred. Generally, one would not expect amounts of MMOH of much less than about 0.03% to give a desired effect on thickening or viscosity-modification. Thus, an overall concentration range for the MMOH of about 0.03% to about 10% is anticipated as being sufficient for most applications.

The functional products into which the MMOH compounds are incorporated are, for the most part, those which rely on water or some aqueous base for avoidance of dryness and, in many cases, to provide fluidity to the formulation. It will be understood, of course, that some products, such as facial cleansing creams, also involve hydrocarbons or other organic compounds emulsified in water, or water emulsified in a hydrocarbon (or organic compound), as a part of the formulation.

Among the cleansers, household products, and personal care products contemplated for use with the MMOH compounds of the present invention are liquid soaps, bar soaps, shampoos, dishwashing detergents, laundry detergents, bleaches, stain removers, tile cleaners, porcelain cleaners, masonry cleaners, floor cleaners, carpet cleansers, toothpaste, denture cleansers, lotions, face creams, grime removers, grease removers, disinfectants, mildew removers, toilet bowl cleansers, grease removers for cook-stoves, mechanic's grease remover, and the like. The MMOH compounds can be used with highly corrosive fluids which are alkaline or have a pH above about 4.5.

The MMOH compounds are beneficially used not only as thickeners or viscosity-modifiers in some products, but also they can, in some instances, stabilize emulsions, cause gelling of the formulation to the consistency of gelatin, and/or suspend particles in a fluid formulation. It is beneficial in many cases that cleansers or other products which are applied to vertical or inclined surfaces be prevented, or at least retarded, from flowing too rapidly off the surface by the force of gravity. This can be the case, for example, when a disinfectant, mildewcide, fungicide, bleach, grime-remover, or the like is sprayed on the walls of a shower bath stall, or sprayed under the inside edge of a toilet bowl, or when a grease-remover is sprayed onto a piece of machinery, or when a mildewcide is sprayed on the wall of a building. In many cases, the product will run off before it can do a thorough job of treating the surface. The present invention offers a remedy for that problem by providing a thickener or viscosity-modifier to cause the product to remain in place long enough to do a more thorough job of alleviating the problem for which it was applied. The thickened product can be easily washed off or hosed off with water after it has been allowed to stand for the desired period of time. The thickening effect can normally be "diluted out" using copious amounts of water.

In the following examples the expression "MAH" is in reference to certain compounds within the generic formula shown above and which conform substantially to the formula $MgAl(OH)_{5-y}Cl_y.xH_2O$ and which are prepared from an aqueous solution containing $MgCl_2$ and $AlCl_3$ as taught, e.g., in U.S. Pat. No. 4,664,843 or in pending Ser. No. 060,133 filed June 9, 1987. The small amount of Cl anion is a residual amount of the $Cl^-$ anion which was in the starting materials.

The following examples are given to illustrate applications of the MMOH in various kinds of products: however, the invention is not limited to only the ones illustrated.

Example 1

A "dry touch" lotion is prepared by admixing the following:

Part A 0.5 parts MAH (dry basis) 85.5 parts water
Part B 0.1 parts triethanolamine 3.5 parts glycerine
Part C 3.6 parts white mineral oil 1.6 parts stearic acid 0.8 parts cetyl alcohol 1.4 parts glycerol monostearate 2.0 parts lanolin The above totals about 99 parts by weight. Mix A until smooth, add B to A and heat to about 70°–75° C. with gentle stirring. Heat C to 75°–80° C. and add C to A/B and mix while cooling. The elevated temperature aids in the blending operation. An emulsion is formed which is thickened and stablilzed by the MAH as observed for several weeks. The so-formed lotion is thixotropic, applies smoothly, and has no greasy feel. Variations in the above formulation can be made and still obtain the beneficial effect of the MAH.

Example 2

A mineral oil emulsion is prepared as follows, all amounts being parts by weight:

Admix about 4.5 parts of flash-dried MAH into about 50 parts of water, add about 41 parts mineral oil and about 3 parts of oleic acid, and stir to produce a thin oil in water emulsion. Addition of about 1 part of $Na_2CO_3$, which produces a thick, stable, creamy emulsion.

Example 3

An antiperspirant is prepared by admixing the following, all amounts being parts by weight.

Part A 1.0 parts of MAH 51.0 parts of water 0.25 parts of NaCl salt*
Part B 8.0 parts glycerol monostearate
Part C 40.0 parts aluminum chlorohydrate (50% aq. soln.)

Mix MAH, salt, and water until smooth. Heat A to 70° C., and heat B to 75° C. Add B To A and mix while cooling to 50° C. Heat C to 50° C. and add C to A/B and mix until cool. A slightly thickened, thixotropic lotion-like stable mixture is obtained which flows easily under shear, such as by rolling or smearing onto the skin.

*The salt can also be KCl, $Na_2SO_4$, $MgCl_2$, or $AlCl_3$; but $Na_2CO_3$, $Na_2HPO_4$, and $NaH_2PO_4$ should not used as these can cause flocculation when aluminum chlorohydrate is in the formulation.

Example 4

An after-shave lotion is prepared as follows, all amounts being parts by weight.

Mix 2.04 parts of dry MAH, 18 parts of ethanol, and 20 parts of deionized water in a sonic blender and add 0.07 parts of $Na_2CO_3$. Then the mixture is mixed in a high-shear mixer and a thick shear-thinning (thixotropic) creamy lotion is produced. Viscosity is measured at various RPM's on a Brookfield viscometer to produce results as follows:

| RPM   | 50  | 1.0   | 0.5               |
|-------|-----|-------|-------------------|
| Visc, | 392 | 7,600 | 20,000 centipoise |

Example 5

A liquid automatic dishwater detergent that dispenses from the container well and substantially remains in the closed cup of a domestic dishwasher is made from the following formulas:

|                              | Formula A | Formula B |
|------------------------------|-----------|-----------|
| MAH aqueous slurry (12.5% MAH) | 104.5 gm  | 125.3 gm  |
| water                        | 83.3 gm   | 62.5 gm   |
| $Na_2CO_3$                   | 20.0 gm   | 20.0 gm   |
| NaOH beads                   | 5.0 gm    | 5.0 gm    |
| sodium silicate 41 Be°       | 167.2 gm  | 167.2 gm  |
| bleach (5.25% NaOCl)         | 300.0 gm  | 300.0 gm  |
| tripolyphosphate             | 300.0 gm  | 300.0 gm  |
| surfactant*                  | 20.0 gm   | 20.0 gm   |

*(the surfactant is disodium 4-decylated oxydibenzenesulfonate.)

The difference between Formulas A and B is that in A the MAH comprises 1.25%, whereas B contains 1.5% MAH. This gives a comparison between two different concentrations of the MAH.

The blending of ingredients is done in an apparatus capable of high shear in viscous blends and has variable speeds, such as that achieved in a Waring blender or a Cowles-type blender.

The MAH slurry and the water are mixed in the mixer at moderate shear until smooth and uniform. The $Na_2CO_3$ is added while stirring and an immediate thickening is observed. Stirring is continued at moderate to high speed until substantially all the $Na_2CO_3$ is dissolved and the thickened slurry is again smooth and uniform. The NaOH is stirred in until dissolved and some thinning is observed. The sodium silicate is added with stirring and more thinning is observed. Stirring is continued until all thickened portions are evenly distributed throughout the system. The bleach is added with stirring and the Na$_5$P$_3$O$_{10}$ (TPP) is added in two portions (200 gm, then 100 gm) taking care to keep the exotherm under control by using a cool bath (excess heat can boil out some water and bleach). The mixture is stirred at high shear until the mixture is smooth, taking adequate time to assure good distribution of undissolved TPP which is present in an amount greater than saturation; this brings the viscosity to near the final point. Reduce the stirring to a level at which there is no vortex and add the surfactant while stirring slowly (to avoid foaming and entrainment of air) until all the surfactant has been added and well distributed.

Tests are made of (1) container dispensability (for ease of getting it out of the bottle) and (2) hot dishwasher closed cup retention and the following data illustrate the findings:

|  | (1) | (2) |
|---|---|---|
| Formula A | 5.18 | 63.5 |
| Formula B | 5.38 | 86.7 |

(1) weight % remaining in dispensing bottle (795 cc bottle with 6.35 mm orifice); reproducibility approx. ±10%.
(2) weight % retained in detergent cup of Kenmore Model 587.1744580 at 118°–122° F. (47.8°–50° C.); reproducibility approx. ±10%.

The dispensing bottle test is done at about ambient temperature. The dishwasher closed cup test is measured before the controls automatically dump the cup into the wash water. The tests indicate the ease with which the liquid dishwasher detergent can be dispensed from a bottle, yet can effectively remain in the closed dishwasher cup until it is ready to be dumped into the water.

By having a liquid detergent which can be thickened enough to remain in the closed cup (which is normally designed to hold powders, thus is not water-tight), yet which will flow out effectively when the cup is opened during the washing cycles, one may avoid having to use powders in the closed cup. The thickened detergent can, of course, also be used in the initial open cup cycle of the dishwasher.

Furthermore, such thickened or gelled liquid detergents can also be used where one wishes to coat a heavily soiled vessel or article (such as a skillet or pan with scorched food in it) with a detergent which does not evaporate very quickly. The thickened detergent can be used to put a thick layer of the detergent on a soiled surface.

Example 6

A consumer product sold for use as a cleanser, known as Tough Act* cleaning solution (a trademark of The Dow Chemical Company), is thickened in accordance with the following recipe:

| Ingredient | Grams | Approx % of Total |
|---|---|---|
| MAH slurry (12% MAH conc.) | 185 | 20.9 |
| Na$_2$CO$_3$ | 6 | 0.7 |
| Tough Act* solution | 693 | 78.4 |
| Totals: | 884 | 100 |

(In the above recipe, the MAH comprises about 2.5 % of the total)

The Na$_2$CO$_3$ is added to the MAH slurry and stirred using a Cowles-type blender until well mixed (about 5 minutes). The Tough Act* solution is added and the mixture is stirred at high speed (but not so fast as to mix in much air and create much foam) until the mixture is smooth (about 5 more minutes).

The following rheological data are obtained using a Brookfield Model RV* viscosimeter (*a trademark):

| RPM: | 0.5 | 1.0 | 2.5 | 5.0 | 10 | 20 | 50 | 100 |
|---|---|---|---|---|---|---|---|---|
| Visc.** | 11.4 | 6.7 | 5.0 | 5.2 | 5.0 | 3.0 | 1.4 | 0.76 |

**viscosity, cps X1000

Thus is it shown that a small % of the MAH thickens the cleaning solution, but it thins easily when sheared. Thus the thickened cleaning solution can be applied to a vertical surface where it does not run off rapidly, or it can be "stacked-up" on a horizontal surface where it does not rapidly evaporate to dryness. This gives the cleaning solution an extended period of contact with the surface, a feature which is helpful if "soaking" of the grime is wanted.

Example 7

Commercially available Kandu* laundry bleach (*a trademark) is thickened in accordance with the following recipe:

| Ingredient | Grams | Approx. % of Total |
|---|---|---|
| MAH slurry (12% MAH conc.) | 418 | 20.9 |
| Na$_2$CO$_3$ | 90 | 4.5 |
| Bleach (5.25% NaOCl) | 1229 | 61.45 |
| Water | 263 | 13.15 |
| Totals: | 2000 | 100 |

(In the above recipe, the MAH comprises about 2.5% of the total and the NaOCl comprises about 3.23% of the total.)

The MAH, Na$_2$CO$_3$ and water are mixed until the Na$_2$CO$_3$ is dissolved and a smooth paste is obtained. The thickened paste is allowed to set for several minutes and the NaOCl solution is added slowly with blending until the mixture is smooth.

The following rheological data are obtained using a Brook-field Model RV* viscosimeter (*a trademark):

| RPM: | 0.5 | 1.0 | 2.5 | 5.0 | 10 | 20 | 50 | 100 |
|---|---|---|---|---|---|---|---|---|
| Visc.** | 26.7 | 19.7 | 12.5 | 7.1 | 3.9 | 2.2 | 1.0 | 0.5 |

**viscosity, cps X1000

Thus is it shown that a small percent of the MAH thickens the bleach solution, but it thins easily when shear. The thickened bleach solution can be applied to a vertical surface where it quickly re-gels and does not run off rapidly, or it can be "stacked-up" on a horizontal surface where it does not rapidly evaporate to dryness. This gives the bleach solution an extended period of contact with the surface, a feature which is helpful when longer periods are wanted or needed, such as when killing mildew or fungus in a shower bath or on a wall, and the like.

Example 8

A small amount of MgAl(OH)$_5$, when added to Easy Off* oven cleaner (*a trademark) thickens it sufficiently that it causes the cleaner to remain on a vertical surface, without running down, for an extended period of time.

Example 9

A small amount (about 2% by weight) of MgAl(OH)$_5$, when added to Tough Act* cleaning solution in a bottle equipped with a hand (or finger) pump for spraying the cleaning solution, thickens the solution sufficiently that it remains in place on a vertical surface when sprayed from the bottle by using the pump, yet the shear acting on the thickened solution by the action of the pump is sufficient to thin it so that it it easily sprayed from the bottle.

Example 10

A small amount of MAH (e.g. about 1-3% by weight), when added to an AFFF* foam preparation (*a tradename of 3M Corporation) used as a foam for fighting fires, has very good stabilizing effect on the foam: the foam lasts longer and clings to vertical surfaces better. Even if the AFFF* foam preparation is made up using sea water instead of plain water, the MAH is effective in its improvement of the foam.

Example 11

In similar manner to the above laundry bleach example, thickened bleaches are prepared by using more MAH and/or by using greater concentrations of NaOCl. Furthermore, other oxidizing or reducing agents are similarly thickened, such as KMnO$_4$, NaCO$_3$, or Na$_2$SO$_3$ and the like, using MAH or other MMOH compounds.

We claim:

1. A method for providing thickening or viscosity-modification of an aqueous-based functional product formulation, said method comprising
adding to the formulation an amount of a mixed metal hydroxide sufficient to thicken the formulation or to modify the viscosity of the formulation, said mixed metal hydroxide being at least one compound conforming substantially to the empirical formula

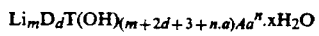

$$\text{Li}_m D_d T(OH)_{(m+2d+3+n\cdot a)} A_a^n \cdot xH_2O$$

where m is an amount of Li of from zero to one,
where D represents at least one divalent metal cation and d is an amount of from about zero to about 4,
where T represents at least one trivalent metal cation,
where A represents at least one monovalent or polyvalent anion or negative-valence radical,
a is an amount of A ions of valence n, with n·a being an amount of from about zero to about −3,
where (m+2d+3+n·a) is equal to or greater than 3.
where (m+d) is greater than zero, and
where xH$_2$O represents excess waters of hydration, with x being zero or more, wherein the formulation is selected from the group consisting of a cleanser, a bleach, a soap, a detergent, a surfactant, shampoo, a toothpaste, a denture cleanser, a lotion, a face cream, an antiperspirant, a disinfectant, a fungicide, a mildewcide, an oxidizing agent, a reducing agent, a dishwasher detergent, or a stain remover.

2. The method of claim 1, wherein the formulation is a cleanser.

3. The method of claim 1, wherein the formulation is selected from the group consisting of a soap, a detergent, and a surfactant.

4. The method of claim 1, wherein the formulation is selected from the group consisting of a bleach, a disinfectant, a fungicide, and a stain remover.

5. The method of claim 1, wherein the formulation is a liquid laundry detergent or dishwasher detergent.

6. The method of claim 1, wherein the formulation is a bleach.

7. The method of claim 1 wherein the M metal is at least one selected from the group consisting of Mg, Ca, Mn, Fe, Co, Ni, Cu, and Zn.

8. The method of claim 1 wherein the M metal is at least one selected from the group consisting of Ca and Mg.

9. The method of claim 1 wherein the T metal is at least one selected from the group consisting of Al, Fe, and Ga.

10. The method of claim 1 wherein the T metal is Al.

11. The method of claim 1 wherein m is zero, d is one, and an is an amount in the range of zero to one.

12. The method of claim 1 wherein A represents at least one inorganic anion or negative-valence radical.

13. The method of claim 1 wherein A represents a hydrophilic organic negative-valence group.

14. The method of claim 1 wherein the A anion represents at least one selected from the group consisting of hydroxyl, halide, sulfate, nitrate, phosphate, carbonate, glycolate, lignosulfate, and polycarboxylic or negative-valence radicals.

15. The method of claim 1, wherein the mixed metal hydroxide is MgAl(OH)(5+n·a)A$_a^n$·xH$_2$O), where n.a is an amount of from zero to one, where A is an anion other than OH— and xH$_2$O is an indefinite amount of excess waters of hydration.

16. The method of claim 15 wherein the A anion is a halide.

17. The method of claim 15 wherein the A anion is chloride.

18. The method of claim 1 wherein the crystalline mixed metal hydroxide is of the monodispersed, monolayer variety.

19. A composition comprising an aqueous-based product formulation which is thickened or viscosity-modified by the presence therein of an effective amount of at least one crystalline mixed metal hydroxide compound conforming essentially to the formula

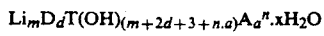

$$\text{Li}_m D_d T(OH)_{(m+2d+3+n\cdot a)} A_a^n \cdot xH_2O$$

where m is from zero to one,
D is a divalent metal and d represents the amount of D,
T is at least one trivalent metal,
A represents at least one monovalent or polyvalent anion or negative-valence radical,
a is an amount of A ions of valence n, with n·a being an amount of from about zero to about −3,
(m+2d+3+n·a) is equal to or greater of than 3,
(m+d) is greater than zero, and
xH$_2$O represents excess waters of hydration, with x being zero or more, wherein the aqueous-based formulation is selected from the group consisting of a cleanser, a bleach, a soap, a detergent, a surfactant, a shampoo, a toothpaste, a denture cleanser, a lotion, a face cream, an antiperspirant, a disinfectant, a fungicide, a mildewcide, an oxidizing agent, a reducing agent, a dishwasher detergent, and a stain remover.

20. The composition of claim 19 wherein the mixed metal hydroxide compound conforms essentially to the formula $$MgAl(OH)_{(5-n.a)}A_a^n \cdot xH_2O$$

where A is chloride and n.a is an amount of from zero to one and x is zero or more.

21. The composition of claim 19 wherein the aqueous-based formulation is a bleach formulation.

22. The composition of claim 19 wherein the aqueous-based formulation is a cleanser.

23. The composition of claim 19 wherein the aqueous-based formulation is a dishwasher detergent or stain remover.

24. The composition of claim 19 wherein the aqueous-based formulation is selected from the group consisting of a disinfectant, fungicide, mildewcide, oxidizing agent, or reducing agent.

25. A method for thickening or viscosity-modifying an aqueous-based functional formulation selected from the group consisting of a cleanser, bleach, a soap, a detergent, a surfactant, a shampoo, a toothpaste, a denture cleanser, a lotion, a face cream, an antiperspirant, a disinfectant, a fungicide, a mildewcide, an oxidizing agent, a reducing agent, a dishwasher detergent, and a stain remover, said method comprising providing an aqueous slurry of crystalline $MgAl(OH)_{(5-n.a)}A_a^n \cdot xH_2O$, where A is at least one anion or negative-valence radical of valence n, and n.a is from zero to $-3$.

adding a small amount of an electrolyte into the slurry and stirring it until the slurry has become thickened and smooth, and to that, adding the aqueous-based functional formulation and stirring until it is well-mixed, thereby obtaining a thickened or viscosity-modified formulation.

26. A method for thickening or viscosity-modifying an aqueous-based functional formulation selected form the group consisting of a cleanser, bleach, a soap, a detergent, a surfactant, a shampoo, a toothpaste, a denture cleanser, a lotion, a face cream, an antiperspirant, a disinfectant, a fungicide, a mildewcide, an oxidizing agent, a reducing agent, a dishwasher detergent, and a stain remover, said method comprising providing an aqueous-based functional formulation having colloidal particles suspended therein in addition to functional components thereof, providing an aqueous slurry of crystalline $MgAl(OH)_{(5-n.a)}A_a^n \cdot xH_2O$, where A is at least one anion or negative-valence radical of valence n, and n.a is from zero to $-3$, mixing together, using shearing forces, the colloidal-containing formulation and the slurry of crystalline material, whereby there is formed an adduct of, or adduct-like union of, the colloidal-material and the crystalline material through a bridging or bonding effect, continuing said mixing, using shearing forces sufficient to expose fresh reaction surfaces on the particles, until the desired thickening or viscosity-modification is obtained.

* * * * *